United States Patent
Kaufhold

[11] Patent Number: 6,166,247
[45] Date of Patent: Dec. 26, 2000

[54] METHOD FOR PREPARING CYCLOPROPANECARBOXYLIC ACIDS

[75] Inventor: Manfred Kaufhold, Marl, Germany

[73] Assignee: Huels Aktiengesellschaft, Marl, Germany

[21] Appl. No.: 09/082,968

[22] Filed: May 22, 1998

[30] Foreign Application Priority Data

May 22, 1997 [DE] Germany .......................... 197 21 426

[51] Int. Cl.$^7$ .................................................. C07C 61/04
[52] U.S. Cl. ............................................ 562/506; 562/400
[58] Field of Search ...................... 562/506, 400

[56] References Cited

U.S. PATENT DOCUMENTS

| | | | |
|---|---|---|---|
| 3,023,183 | 2/1962 | Nelson | 524/742 |
| 4,683,089 | 7/1987 | Leigh | 562/506 |

OTHER PUBLICATIONS

Kirk–Othmer, Esterification, Encyclopedia of Chemical Tech., pp. 307–308, Apr. 1980.

Friedhelm Korte, Georg Thieme Verlag, Stuttgart, pp. 563–564, "Methodicum Chimicum [Latin: Chemical Methods]", 1975.

*Primary Examiner*—Gary Geist
*Assistant Examiner*—Taylor V. Oh
*Attorney, Agent, or Firm*—Oblon, Spivak, McClelland, Maier & Neustadt, P.C.

[57] ABSTRACT

The invention relates to a novel method for preparing cyclopropanecarboxylic acids by acidolysis of the corresponding esters, using an alkylbenzenesulfonic acid represented by the formula:

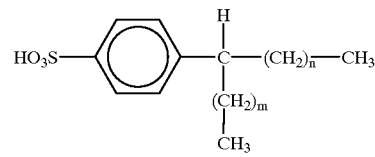

as the reaction catalyst, where m+n is 5 to 15. Process-engineering improvements and simplifications are achieved with this process.

12 Claims, No Drawings

METHOD FOR PREPARING CYCLOPROPANECARBOXYLIC ACIDS

BACKGROUND OF THE INVENTION

1. Field of the Invention

The present invention relates to a method for preparing cyclopropanecarboxylic, acids by acidolysis of the corresponding esters according to the following scheme:

$$\text{(1)} \quad R_1 \overset{R^3}{\underset{R_2}{\triangle}} \overset{COOR_7}{R_4} + R_6COOH \longrightarrow$$

$$\text{(2)}$$

$$R_1 \overset{R^3}{\underset{R_2}{\triangle}} \overset{COOH}{R_5} + R_6COOR_7$$

$$\text{(3)} \qquad \qquad \text{(4)}$$

using an alkylbenzenesulfonic acid as the reaction catalyst, where $R_1$, $R_2$, $R_3$ are each, independently, H, $C_1$- to $C_4$-alkyl, or phenyl, $R_4$ is H or $COOR_7$, $R_5$ is H, $COOR_7$, or COOH, $R_6$ is H, $CH_3$, $C_2H_5$, or $C_3H_7$, $R_7$ is $CH_3$ or $C_2H_5$.

2. Description of the Background

Cyclopropanecarboxylic acids are important intermediates in the preparation of a variety of asymmetric chemicals, pharmaceutical products and crop protection agents.

The cyclopropanecarboxylic acid esters (1) are prepared by known methods. The methyl cyclopropanecarboxylate is synthesized, for example, by reacting methyl 4-chlorobutyrate with sodium methylate, according to EP-A-0 577 949, incorporated herein by reference.

The literature also discloses syntheses of cyclopropanecarboxylic acids (3). For example, Org. Synth. Coll. Vol. 3 (1955), 221, describes the alkaline saponification of the corresponding nitrile. This method gives rise to ammonia and alkali metal salts as waste products in stoichiometric amounts, which have to be disposed of.

The alkaline saponification of cyclopropanecarboxylic acid esters likewise encounters the problem of salt being produced in stoichiometric amounts.

With acidolysis, in contrast, less salt is produced, since this method makes use of catalysis. Detailed descriptions of the acidolysis are found in textbooks, e.g. in Organikum, 20th edition, Johann Ambrosius Barth Verlag (1996), 459. This recommends sulfuric acid as the catalyst and formic acid as the carboxylic acid.

In the case of the cyclopropanecarboxylic acids, such acidolysis requires relatively large amounts of sulfuric acid. Furthermore, this acid has to be neutralized, for example with sodium hydroxide solution, after the reaction since the sensitive cyclopropanecarboxylic acids are otherwise decomposed when they are worked up by distillation. This procedure therefore likewise gives rise to quantities of salts which have to be separated off and disposed of.

All the known methods for preparing cyclopropanecarboxylic acids therefore have in common that they consume large amounts of chemicals, thus leading to waste disposal problems.

SUMMARY OF THE INVENTION

It is an object of the present invention to prepare cyclopropanecarboxylic acids while avoiding the abovementioned drawbacks.

This object is achieved, surprisingly, by employing as the catalyst in the acidolysis an alkylbenzenesulfonic acid of the formula $$HO_3S-\bigcirc-\overset{H}{\underset{(CH_2)_m}{\underset{|}{C}}}-(CH_2)_{\overline{n}}-CH_3$$
$$\underset{CH_3}{|}$$

where m+n is 5 to 15.

Accordingly, the present invention provides a method for preparing a cyclopropanecarboxylic acid represented by formula (3):

$$R_1 \overset{R^3}{\underset{R_2}{\triangle}} \overset{COOH}{R_5} \quad (3)$$

by catalyzing the reaction of a cyclopropanecarboxylic acid ester represented by formula (1) and a carboxylic acid represented by formula (2):

$$R_1 \overset{R^3}{\underset{R_2}{\triangle}} \overset{COOR_7}{R_4} \quad (1)$$

$$R_6COOH \quad (2)$$

with an alkylbenzenesulfonic acid represented by the formula:

$$HO_3S-\bigcirc-\overset{H}{\underset{(CH_2)_m}{\underset{|}{C}}}-(CH_2)_{\overline{n}}-CH_3$$
$$\underset{CH_3}{|}$$

to produce the cyclopropanecarboxylic acid represented by formula (3) and a carboxylic acid ester represented by the formula (4): $R_6COOR_7$,
where:

$R_1$, $R_2$, $R_3$ are each, independently, H, $C_1$- to $C_4$-alkyl, or phenyl, $R_4$ is H or $COOR_7$, $R_5$ is H, $COOR_7$, or COOH, $R_6$ is H, $CH_3$, $C_2H_5$, or $C_3H_7$, $R_7$ is $CH_3$ or $C_2H_5$, and m+n is 5 to 15.

A more complete appreciation of the invention and many of the attendant advantages thereof will be readily obtained as the same becomes better understood by reference to the following detailed description.

DETAILED DESCRIPTION OF THE INVENTION

While the reaction does not require a solvent, it is possible, e.g., when dealing with a solid, to add solvent of a suitable boiling point. The important point is that it should be possible for the ester (4) formed to be readily separated off from the reaction mixture, for example, by distillation, so that the equilibrium is thus rapidly shifted in the desired direction. Only the methyl and ethyl esters are therefore used (i.e., $R_7$ is $CH_3$ or $C_2H_5$), with preference being given to the use of the methyl esters.

In addition, the carboxylic acids represented by formula (2) preferably have low boiling points, such as formic, acetic, propionic and butyric acids, with formic acid being preferred. For economic reasons, the carboxylic acid (2) is generally used in excess with respect to the ester (1).

The alkylbenzenesulfonic acids employed as the catalyst have a straight-chain or branched alkyl radical in the 4-position, which preferably has from 10 to 13 carbon atoms. Examples include a tetrapropyl, n-decyl, n-undecyl, n-dodecyl and n-tridecyl side chain. For economic reasons, it is especially preferred to use those alkylbenzenesulfonic acids which comprise customary, industrially readily preparable and readily available mixtures.

The catalyst is added in relatively large amounts of preferably from 5 to 50 wt %, based on the ester (1), special preference being given to the use of amounts of from 7 to 15 wt %. These ranges include all specific values and subranges therebetween, including 10, 20, 25, 30, 35, 40, and 45 wt %, based on the weight of ester (1).

In an especially preferred embodiment of the invention, the reaction products are distilled off after the reaction, whereupon the liquid bottom product is reused as the catalyst for the next reaction.

This method of the present invention is made possible by the stable alkylbenzenesulfonic acid catalyst. The reason is that, even though relatively large amounts of alkylbenzenesulfonic acid are used, there is no significant decomposition, which would lead either to low-boiling components or to high-boiling components which cannot be distilled and would not be able to be separated off from the alkylbenzenesulfonic acid. The catalyst can therefore be recycled very many times. The catalyst does not have to be disposed of.

This makes the method economical and readily manageable on an industrial scale. By virtue of the high catalyst concentration used, the reaction also proceeds rapidly and completely.

These effects could not have been foreseen.

In ester (1) the $R_1$, $R_2$ and $R_3$ groups may be the same or different. These groups may be bonded to the two carbon atoms which are not substituted by —$COOR_7$ and —$R_4$ in any configuration. In one embodiment, $R_1$, $R_2$ and $R_3$ are each a hydrogen atom.

$R_4$ in formula (1) may be hydrogen or —$COOR_7$. When $R_4$ is hydrogen, then $R_5$ in acid (3) is also hydrogen. Preferably, $R_4$ is hydrogen.

In practice, the method is implemented, for example, as follows. The cyclopropanecarboxylic acid ester (1) and the carboxylic acid (2) are introduced as the initial charge, the molar ratio being from 1:1 to 1:20, preferably from 1:1.1 to 1:10 and particularly preferably from 1:1.1 to 1:3. These ranges include all specific values and subranges therebetween. Then the catalyst is added and the mixture is heated with stirring. The reaction generally takes place at from 90 to 150° C., including all temperatures in between and subranges thereof. The ester (4) is distilled off in the process, a further option being that of applying a slight vacuum in the range of from 500 to 1000 hPa. It is also possible to use a column with the distillation, to avoid distillation of the ester (1). When the reaction is complete, the overhead temperature in the distillation will rise.

Then the reaction mixture is distilled off (topped) from the catalyst and the liquid distillation residue is introduced into the next reaction. The reaction mixture distilled off is worked up by customary methods, for example by distillation in the case of the liquid cyclopropanecarboxylic acid (3) or by filtration and recrystallization in the case of solid carboxylic acids (3).

The method can also be implemented continuously. In this case for example formic acid, ester and catalyst are introduced as the original charge, a mixture of formic acid, catalyst and ester is added with heating, methyl formats is distilled off and bottom product is drawn off evenly from the reactor and this mixture is worked up continuously or batchwise.

Having generally described this invention, a further understanding can be obtained by reference to certain specific examples which are provided herein for purposes of illustration only and are not intended to be limiting unless otherwise specified.

EXAMPLES

Example 1

Use is made of a glass apparatus which consists of a four-necked flask with stirrer, thermometer, dropping funnel, distillation column fined with distillation bridge, and receiver.

The initial charge comprises:

750 g (7.5 mol) of methyl cyclopropanecarboxylate (MCPC)

521 g (11.3 mol) of formic acid 75 g of $C_{10}$- to $C_{13}$-alkylbenzenesulfonic acid (MAARLON®) AS 3 acid).

The products are combined and heated to above 105° C. The methyl formats produced is distilled off, the bottom temperature being increased accordingly, to about 130° C. The overhead temperature is 38° C. After 7.5 h, the reaction is complete. The MCPC content is 0.5%.

The reaction mixture is freed from catalyst by topping on a distillation bridge at 133 hPa. This affords 77 g of distillation residue and 775 g of distillate, i.e., no appreciable amounts of nondistillable high-boiling components are formed. The residue is reused as catalyst.

The topped production mixture is subjected to fractional distillation, 587 g of cyclopropanecarboxylic acid (CPC) having a purity of 99.4% being obtained. The yield of CPC is calculated at about 90%, based on MCPC used.

Comparative Example

The apparatus described in Example 1, and the amounts of MCPC and formic acid specified therein, are used, and 30 g of cone, sulfuric acid are added as the catalyst. This mixture is heated to above 100° C. Distillation of the methyl formats commences at 102° C. After the reaction, the mixture is cooled and, to neutralize the sulfuric acid, 20.4 g of 50% strength sodium hydroxide solution are added to the bottom product. This is followed by direct distillation under reduced pressure, CPC being obtained in a yield of 87%.

This distillation produces 95 g of a partially solid residue which is dissolved in 150 ml of water. This solution contains about 10% of CPC, and the carbon content is 7.5%. This waste cannot be disposed of as such, but has to be worked up first by extraction or distillation.

German Patent Application 197 21 426.6, filed May 22, 1997, is incorporated herein in its entirety.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for preparing a cyclopropanecarboxylic acid represented by formula (3):

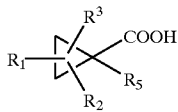
(3)

comprising catalyzing the reaction of a cyclopropanecarboxylic acid ester represented by formula (1) and a carboxylic acid represented by formula (2):

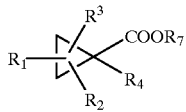
(1)

(2)

with an alkylbenzenesulfonic acid represented by the formula:

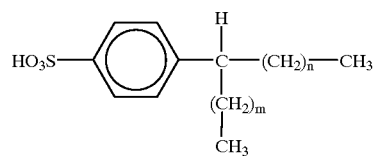

to produce the cyclopropanecarboxylic acid represented by formula (3) and a carboxylic acid ester represented by the formula (4): $R_6COOR_7$,
wherein
$R_1$, $R_2$, $R_3$ are each, independently, H, $C_1$- to $C_4$-alkyl, or phenyl,
$R_4$ is H or $COOR_7$,
$R_5$ is H, $COOR_7$, or COOH,
$R_6$ is H, $CH_3$, $C_2H_5$, or $C_3H_7$,
$R_7$ is $CH_3$ or $C_2H_5$, and
m+n is 5 to 15.

2. The method of claim 1, wherein m+n is 7 to 10.

3. The method of claim 1, wherein the amount of the alkylbenzenesulfonic acid used is from 5 to 50 wt %, based on the amount of the cyclopropanecarboxylic acid ester represented by formula (1).

4. The method of claim 1, which is conducted at 90 to 150° C.

5. The method of claim 1, further comprising distilling the product of the catalyzing step to produce a residue containing the alkylbenzenesulfonic acid, followed by recycling the residue to another catalyzing step.

6. The method of claim 1, wherein $R_4$ and $R_5$ are each H.

7. The method of claim 1, wherein $R_1$, $R_2$ and $R_3$ are each H.

8. The method of claim 1, wherein $R_7$ is $CH_3$.

9. The method of claim 1, wherein $R_7$ is $C_2H_5$.

10. The method of claim 1, wherein $R_6$ is H.

11. The method of claim 1, wherein $R_6$ is $CH_3$, $C_2H_5$, or $C_3H_7$.

12. The method of claim 1, wherein the carboxylic acid ester represented by the formula (4) produced in the catalyzing step is removed from the reaction mixture.

* * * * *